(12) United States Patent
Wyman et al.

(10) Patent No.: US 10,815,163 B2
(45) Date of Patent: Oct. 27, 2020

(54) SYSTEMS FOR REDUCING RESOURCE CONSUMPTION IN PRODUCTION OF ALCOHOL FUEL BY CONVERSION TO HYDROCARBON FUELS

(71) Applicant: Vertimass, LLC, Irvine, CA (US)

(72) Inventors: Charles E. Wyman, Riverside, CA (US); John R. Hannon, Salem, NH (US)

(73) Assignee: Vertimass, LLC, Irvine, CA (US)

( * ) Notice: Subject to any disclaimer, the term of this patent is extended or adjusted under 35 U.S.C. 154(b) by 0 days.

(21) Appl. No.: 16/418,765

(22) Filed: May 21, 2019

(65) Prior Publication Data

US 2019/0337867 A1 Nov. 7, 2019

Related U.S. Application Data

(62) Division of application No. 15/179,479, filed on Jun. 10, 2016, now Pat. No. 10,315,965.

(60) Provisional application No. 62/184,142, filed on Jun. 24, 2015, provisional application No. 62/174,672, filed on Jun. 12, 2015.

(51) Int. Cl.
  *B01D 3/00* (2006.01)
  *C10G 3/00* (2006.01)
  *C07C 1/20* (2006.01)

(52) U.S. Cl.
  CPC .............. *C07C 1/20* (2013.01); *B01D 3/002* (2013.01); *C10G 3/42* (2013.01); *C10G 2300/202* (2013.01); *C10G 2300/40* (2013.01); *C10G 2300/4006* (2013.01); *C10G 2400/02* (2013.01); *C10G 2400/04* (2013.01); *C10G 2400/08* (2013.01); *C10G 2400/30* (2013.01); *Y02P 30/20* (2015.11)

(58) Field of Classification Search
  CPC .... C07C 1/20; C10G 3/42; C10G 2300/1014; B01D 3/002; B01D 3/007; Y02P 30/20
  See application file for complete search history.

(56) References Cited

U.S. PATENT DOCUMENTS

| | | | |
|---|---|---|---|
| 4,621,164 A | 11/1986 | Chang et al. | |
| 5,135,861 A | 8/1992 | Pavilon | |
| 2005/0069998 A1 | 3/2005 | Ballesteros et al. | |
| 2010/0174127 A1 | 7/2010 | Chang | |
| 2012/0323055 A1 | 12/2012 | Gruber | |

OTHER PUBLICATIONS

Aden, Andy; Water Usage for Current and Future Ethanol Production; National Renewable Energy Laboratory; Sep./Oct. 2007 • Southwest Hydrology.

*Primary Examiner* — Lessanework Seifu
(74) *Attorney, Agent, or Firm* — Fish IP Law, LLP (57) ABSTRACT

Systems are presented that reduce energy and water consumption in processes for producing fuel from renewable alcohol-containing feedstreams. Alcohol content is converted directly to hydrocarbon transport fuels in a catalytic process, with heat transferred between intermediate process streams to reduce heat energy consumption. Overall water consumption is reduced by recovery of water from the catalytic process and reduction of water temperature to reduce evaporative losses.

21 Claims, 4 Drawing Sheets

FIG. 4 ial Patent Application No. 62/184,142, filed Jun. 24, 2015 and U.S. Provisional Patent
SYSTEMS FOR REDUCING RESOURCE CONSUMPTION IN PRODUCTION OF ALCOHOL FUEL BY CONVERSION TO HYDROCARBON FUELS This application is a divisional application of U.S. patent application Ser. No. 15/179,479, filed Jun. 10, 2016, which claims the benefit of U.S. Provisional Patent Application No. 62/184,142, filed Jun. 24, 2015 and U.S. Provisional Patent Application No. 62/174,672, filed Jun. 12, 2015. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is the conversion of alcohol from renewable sources into hydrocarbon fuels.

BACKGROUND

The background description includes information that may be useful in understanding the present invention. It is not an admission that any of the information provided herein is prior art or relevant to the presently claimed invention, or that any publication specifically or implicitly referenced is prior art.

Ethanol is currently receiving a great deal of interest as a renewable source of alternative transport fuel, with over 23 billion gallons (87 billion liters) of ethanol produced for fuel purposes in 2014 worldwide. Ethanol is typically derived via a fermentation process (for example, corn ethanol fermentations) and then concentrated via distillation and molecular sieves to produce a fuel grade product. Unfortunately, the formation of ethanol/water azeotropes for which the composition of the liquid and vapor are identical complicates recovery of high purity ethanol. As a result, removal of ethanol from fermentation broths to produce high purity ethanol suitable for use as a fuel or in fuel mixtures frequently requires processing through energy-intensive distillation steps that include application of energy-intensive processes that specifically remove water from azeotropic mixtures. These additional steps significantly impact the costs of producing fuel-grade ethanol, lower potential greenhouse gas reductions, and cast doubts on the sustainability of ethanol as a renewable fuel.

There are a number of shortcomings to the use of ethanol as a fuel. For example, significant adaptation of internal combustion engines is necessary to permit them to use ethanol as a fuel. Another factor is that ethanol is not truly fungible with conventional hydrocarbon fuels. For example, current infrastructures do not support transportation of ethanol via pipelines, but rather using tanker trucks and trains. Ethanol also has two-thirds the energy density of gasoline, which results in up to 50% more ethanol being needed to travel the same distance as gasoline. Because of differences in the properties of gasoline and ethanol most current vehicles are not warranted to use ethanol/gasoline blends containing more than 10% ethanol, while the existing infrastructure is limited to using up to 85% ethanol in gasoline (i.e. E85 fuel blend). The lower energy density and hygroscopic nature of ethanol prevent its use in aircraft that look to maximize energy content per mass of fuel and minimize water retention in the fuel. In addition, ethanol is not well suited for use in diesel engines in heavy-duty vehicles.

In addition to providing low energy density, production of fuel-grade ethanol from renewable sources (such as fermentation products) has relatively high energy requirements. Ethanol feedstocks provided from renewable sources typically has a high water content, which must be removed prior to use as fuel. At large scales this is typically achieved using one or more distillation processes, which have significant heat requirements. The limitations of ethanol distillation due to the formation of ethanol:water azeotropes necessitate the use of additional steps, such as the application of molecular sieves, to produce ethanol that is sufficiently anhydrous for fuel use. The regeneration of such molecular sieve materials constitutes an additional energy expenditure.

In addition to high energy costs the production of fuel grade ethanol from renewable sources also consumes considerable fresh water. While approximately 96% of the corn currently used for ethanol production is grown without irrigation (see Aden, A. "Water Usage for Current nd Future Ethanol Production", Southwest Hydrology, September/October 2007, pp: 22-23) and ethanol plants generally recover much of their processing water, significant water consumption occurs in boiler systems and cooling towers. Estimates are that between 3 and 4 gallons of water are consumed for every gallon of ethanol produced from fermentation of corn. All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply. Water consumption is greater in biochemical conversion of cellulosic feedstocks to ethanol, averaging approximately 6 gallons of water for every gallon of ethanol produced. Water consumption for thermochemical conversion of cellulosic biomass to ethanol averages 1.9 gallons of water per gallon of ethanol. Most of this fresh water is sourced from groundwater.

Thus, there remains a need for systems and methods that reduce the energy and water requirements of processes producing alcohol fuels from the output of fermentation processes.

SUMMARY OF THE INVENTION

The inventive subject matter provides apparatus, systems and methods in which energy and water requirements of a plant producing fuel from an alcohol-containing feedstream are reduced. The alcohol-containing feedstream is directed through a catalytic process that produces energy dense hydrocarbon fuels. Energy requirements are reduced or eliminated by transferring heat between intermediate process and/or product streams and by combustion of light hydrocarbon products. Water requirements are reduced by recovery of water generated by the catalytic process and cooling of water streams to reduce evaporation.

One embodiment of the inventive concept is a method for producing a hydrocarbon product. In such a method an alcohol broth is supplied to a primary beer column preheater (and in some instances a second beer column preheater) to generate a heated alcohol broth, which is transferred to a beer column. The beer column produces a first intermediate product stream (which includes an alcohol/water mixture) and a second intermediate product stream (which includes residual solid matter). The first intermediate product stream is directed to a reactor pre-heater to produce a pre-heated first intermediate product stream having a temperature of at least about 220° C. In some embodiment all or part of the second intermediate product stream is returned to the beer column. The pre-heated first intermediate product stream is directed to a furnace to produce a heated first intermediate product stream having a temperature of at least about 250° C. The heated first intermediate product stream is directed to a catalytic reactor, which generates a third intermediate product stream that includes a hydrocarbon product, water and a light hydrocarbon. This third intermediate product stream is directed to a phase separator along a heat transfer route, which is arranged to transfer at least a portion of heat energy of the third intermediate product stream to the reactor pre-heater and/or the primary beer column pre-heater. The phase separator separates the third intermediate product stream into a hydrocarbon product (which is collected and includes the hydrocarbon product), a water stream, and a light hydrocarbon fraction stream. In some embodiments the light hydrocarbon fraction stream is transferred to the furnace for use as a fuel, which can be replaced or supplemented by natural gas. In some embodiments the water stream is used in a fermentation process. The hydrocarbon product can be gasoline, diesel fuel, jet fuel, chemicals, or a BTX product. In such embodiments the energy supplied to the method in the production of a volume of the hydrocarbon product represents less than 20% of energy obtained by combustion of the volume of the hydrocarbon product.

Another embodiment of the inventive concept is a system for carrying out the method described above. Such a system includes a source of alcohol broth which is in fluidically connected to a primary beer column pre-heater (which can, in turn, be connected to a second beer column pre-heater). The system also includes a beer column that receives a heated ethanol broth from the primary beer column pre-heater and produces a first intermediate product stream (which includes an alcohol/water mixture) and a second intermediate product stream (which includes residual solid matter). The system also includes a reactor pre-heater that is fluidically connected to the beer column and that receives the first intermediate product stream, heating it to produce a pre-heated first intermediate product stream. The system also includes a furnace that is fluidically connected with the reactor pre-heater and that receives the pre-heated first intermediate product stream, heating it to at least about 250° C. to produce a heated first intermediate product stream. The system also includes a catalytic reactor that is fluidically connected to the furnace and that generate a third intermediate product stream, which includes a hydrocarbon product, water, and a light hydrocarbon. Such a system also includes a first conduit that is positioned to direct the third intermediate product stream to a phase separator, and to transfer at least some of the heat energy of the third intermediate product stream to the reactor pre-heater (and, in some embodiments, the primary beer column pre-heater). The phase separator separates the third intermediate product stream into a hydrocarbon product stream (which includes a hydrocarbon product), a water stream (which can be directed to a fermentation process), and a light hydrocarbon fraction stream. The hydrocarbon product can be gasoline, diesel fuel, jet fuel, chemicals, and/or a BTX product. In some embodiments the system includes a second conduit that is fluidically connected to the phase separator and positioned to direct the light hydrocarbon fraction stream to the furnace. In other embodiments this can be replaced or supplemented by a source of natural gas. In some embodiments the system includes a third conduit that is fluidically connected to the beer column, and is positioned to direct at least part of the second intermediate process stream back to the beer column. In some embodiments the energy supplied to the system to produce a given volume of the hydrocarbon product represents less than 20% of energy obtained on combustion of the volume of hydrocarbon product.

Another embodiment of the inventive concept is a method for reducing water consumption in a fuel plant. In such a method an alcohol broth (which includes an alcohol is obtained and transferred to a primary beer column pre-heater (and in some embodiments to an additional secondary beer column pre-heater), where it is heated to produce a heated alcohol broth. The heated alcohol broth is transferred from the primary beer column pre-heater to a beer column, which generates a first intermediate product stream (which includes a concentrated alcohol/water mixture). The concentrated alcohol/water mixture is transferred to a catalytic unit pre-heater, which generates a pre-heated alcohol/water mixture. The pre-heated alcohol/water mixture is transferred to an oven, which generates a heated alcohol/water mixture. The heated alcohol/water mixture is transferred to a catalytic unit, which generates a second intermediate product stream that includes water and a hydrocarbon product (and, in some embodiments, a light hydrocarbon). In some embodiments this catalytic step generates at least one mole of water for every mole of alcohol that is converted into hydrocarbons. The second intermediate product stream is transferred to a phase separator, which separates it into a hot water stream and a hydrocarbon product stream (and, in some embodiments, a light hydrocarbon stream). The hot water stream is then recycled into either or both of a fermentation process or a fuel generating process. In some embodiments heat from the hot water stream can be transferred to the secondary beer column pre-heater, which can be supplemented with heat transferred from the second intermediate product. Such heat transfer processes can reduce the temperature of the hot water stream. In some embodiments of the inventive concept the hot water stream is cooled (for example by at least 30° C.) to produce a cooled water stream. This cooling can be accomplished using a passive device (such as a radiator) or an active device (such as an absorption cooler). In some embodiment such an active device can be powered by heat that is transferred from the second intermediate product stream. In some embodiments, the light hydrocarbon stream can be utilized as fuel for the furnace.

Another embodiment of the inventive concept is a system for reducing water consumption in a fuel plant. Such a system includes a source of an alcohol broth comprising ethanol and a primary beer column pre-heater that is fluidically connected to the source of alcohol broth, and in some embodiments a secondary beer column pre-heater that is fluidically connected to this primary beer column pre-heater. The system also includes a beer column that is fluidically connected to the primary beer column pre-heater, and which produces a first intermediate product stream that includes a concentrated alcohol/water mixture. The system also includes a catalytic unit pre-heater that is fluidically connected to the beer column, and that receives the concentrated alcohol/water mixture to produce a pre-heated alcohol/water mixture. The system also includes an oven that is fluidically connected to the catalytic unit pre-heater, which receives the pre-heated alcohol/water mixture and produces a heated alcohol/water mixture. The system also includes a catalytic unit that is fluidically connected to the oven, and which and that receives the heated alcohol/water mixture and produces a second intermediate product stream which includes water and a hydrocarbon product (and, in some embodiments, light hydrocarbons). Such a catalytic unit can produce at least 1 mole of water for every mole of alcohol that is converted to hydrocarbon product. The system also includes a phase separator that is fluidically connected to the catalytic unit and that receives the second intermediate product stream, and which separate the second intermediate product stream into a hot water stream, a hydrocarbon product stream, and (in some embodiments) a light hydrocarbon stream. Such a system includes a first conduit that is fluidically connected to the phase separator and which carries the hot water stream for recycling. Such a first conduit can be positioned to transfer heat from the hot water stream to a beer column pre-heater (for example, a secondary beer column pre-heater). In some embodiments the system includes a cooling unit that is fluidically connected to the first conduit and that provides a cooled water stream. Such a cooling unit can be a passive device (such as a radiator) or an active device (such as an absorption cooler). In some embodiments the system includes a second conduit that is fluidically connected to the catalytic reactor and to the phase separator, and which serves to transfer the second intermediate product from the catalytic reactor to the phase separator while transferring at least part of the heat contained in the second intermediate product to such an active cooling device. In some embodiments the system includes a third conduit that is fluidically connected to the phase separator and to the oven, and which serves to transfer the light hydrocarbon stream from the phase separator to the oven. In some embodiments the system includes a fourth conduit that is fluidically connected to the catalytic unit and the phase separator and that receives the second intermediate product stream from the catalytic unit. In such an embodiment the fourth conduit is positioned to transfer heat energy contained in the second intermediate product stream to a beer column pre-heater (such as the secondary beer column pre-heater).

Various objects, features, aspects and advantages of the inventive subject matter will become more apparent from the following detailed description of preferred embodiments, along with the accompanying drawing figures in which like numerals represent like components.

DETAILED DESCRIPTION

The following description includes information that may be useful in understanding the present invention. It is not an admission that any of the information provided herein is prior art or relevant to the presently claimed invention, or that any publication specifically or implicitly referenced is prior art.

The inventive subject matter provides apparatus, systems and methods in which an alcohol/water vapor mixture, for example a mixture obtained from a location downstream of a fermentation process (e.g., as a feedstream from a beer column, rectification column, molecular sieves), is catalytically reacted to produce hydrocarbon products and water. The catalytic process converts at least a portion of the ethanol of such an alcohol/water vapor mixture into a mixture that includes hydrocarbon fuels and/or other chemicals such as BTX (benzene, toluene, and/or xylene) and water, from which the targeted products are readily separated from water and/or any gaseous byproducts (for example, light hydrocarbons derived from ethanol). Exemplary reactions of this process for various alcohols are shown below in Formulas 1 to 4, where —$C_2H_4$— represents a hydrocarbon (for example, hydrocarbons of a hydrocarbon fuel).

$2CH_3OH \rightarrow$ —$C_2H_4$— $+2H_2O$ (Conversion of methanol to hydrocarbons and water)  Formula 1

$C_2H_5OH \rightarrow$ —$C_2H_4$— $+H_2O$ (Conversion of ethanol to hydrocarbons and water)  Formula 2

$2C_3H_7OH \rightarrow 3$—$C_2H_4$— $+2H_2O$ (Conversion of propanol to hydrocarbons and water)  Formula 3

$C_4H_9OH \rightarrow 2$—$C_2H_4$— $+H_2O$ (Conversion of butanol to hydrocarbons and water)  Formula 4

Water recovered from this reaction can be re-utilized to reduce water losses associated with corn or cellulosic ethanol production facilities (for example, evaporative losses in cooling tower, solids drying, boiler system, etc.) and/or reutilized in feedstock irrigation. In addition, heat provided by combustion of light hydrocarbon products of the catalytic reaction and heat generated by the ethanol conversion process can be transferred to and utilized in ethanol production and recovery processes (for example, in beer column and/or rectification column reboilers) to reduce energy costs in a more carbon-neutral manner.

Heat provided by combustion of light hydrocarbon products of the catalytic reaction and heat generated in the ethanol conversion process are transferred to and utilized in various processes of the plant, thereby reducing energy costs in a carbon-neutral manner.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

One should appreciate that the disclosed systems and methods provide many advantageous technical effects including providing a continuous process for conversion of corn, sugar, or lignocellulose-derived alcohols to high energy density transportation fuels and/or BTX products while providing reduced costs, power consumption, water consumption, and carbon footprint.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Production of fuel from grain sources, for example corn, generally begins with fermentation and provides such fuel in the form of an alcohol (e.g., ethanol, propanol, and/or butanol,). A workflow for a typical prior art process is shown below in FIG. 1.

Figure 1:
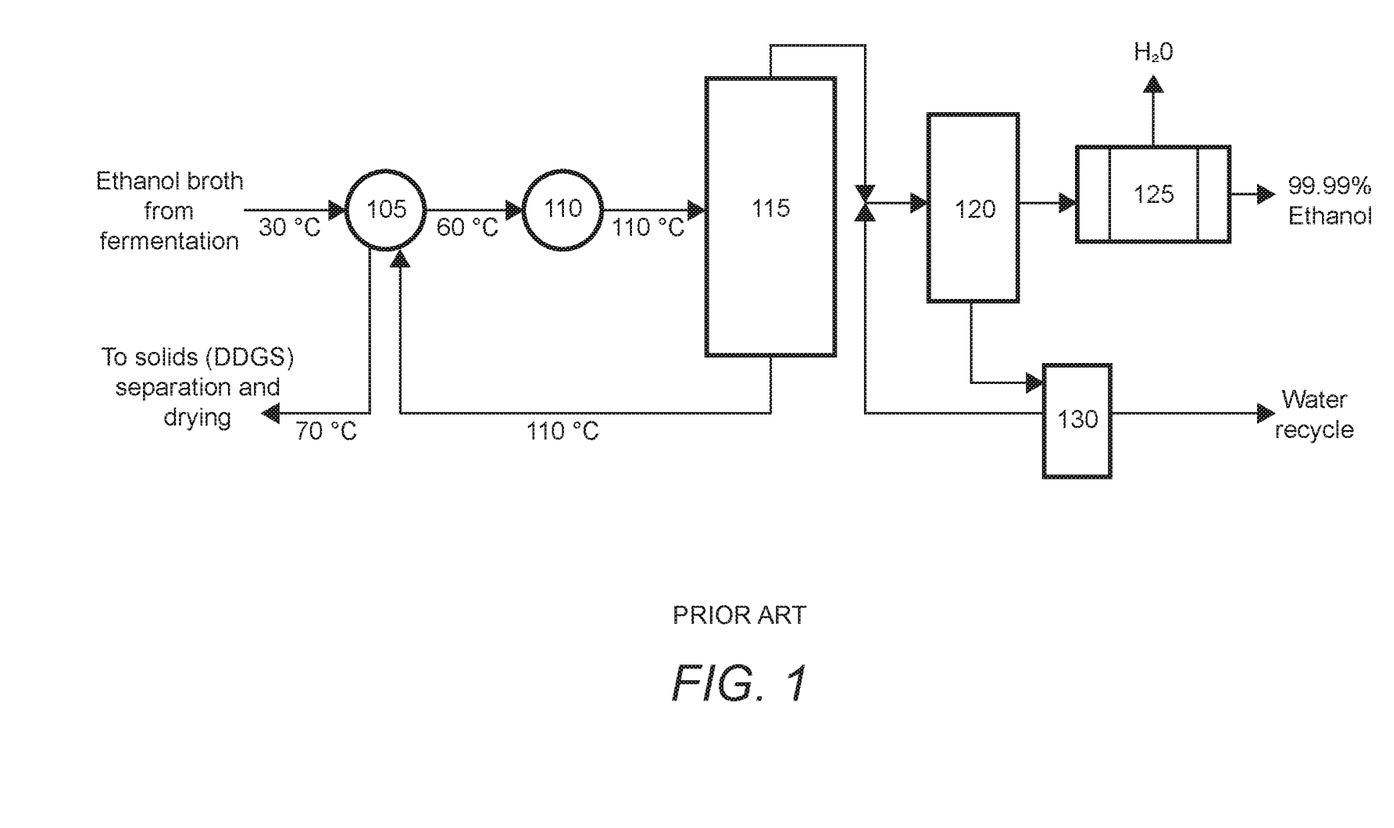
FIG. 1 schematically depicts a typical prior art process for dry mill production of alcohol fuel via grain fermentation.

FIG. 1 schematically illustrates a typical prior art grain dry mill fermentation to ethanol fuel process, an ethanol broth exiting fermentation is first heated in a beer column pre-heater 105 through heat exchange with the bottoms stream from the beer column 115. After this heat exchange, solids from this bottoms stream are removed (for example by centrifugation or filtration), dried, and sold as dried distillers grains (DDGs). In some prior art processes a supplemental heater 110 is used to further increase the temperature of the ethanol broth. The pre-heated ethanol broth is then transferred to a beer column 115, where ethanol is stripped from the ethanol broth to create a concentrated ethanol/water mixture that typically contains 40-60% ethanol (w/w). This transfer of heat from the bottoms stream to the beer column pre-heater 105 lowers process heating/energy requirements by heat integration. The ethanol/water vapor mixture from the beer column is transferred to a rectification column 120, where distillation of the ethanol/water mixture (typically ~40-60% alcohol (w/w) on entry to the rectification column) provides further separation of ethanol from the water mixture and produces a high ethanol content fraction. The high ethanol content fraction is subsequently passed through molecular sieves 125 to generate high purity ethanol that can be used as a transport fuel (albeit, one with lower energy density compared to conventional gasoline). The bottoms stream from the rectification column (having a low percent ethanol content) is transferred to a stripper 130, which separates most of the remaining ethanol and returns it to the rectification column 120 for additional processing. Water from the stripper 130 can be recycled for use in fermentation and other processes.

It should be appreciated that energy consumption by various components of such a system are significant. For a typical plant, the energy consumption per gallon of fuel ethanol produced is as follows: beer column pre-heater ~3,000 BTU, beer column ~20,000 BTU, rectification column ~7,000 BTU, molecular sieve ~2,000 BTU, and stripper ~1,000 BTU. This energy can be provided by burning fossil fuels (such as natural gas), which negatively impacts the carbon footprint of this process. Alternatively, such steps could be fueled using a portion of the ethanol product, but at the cost of process efficiency.

It should be noted that the ~33,000 BTU that are utilized to produce one gallon of ethanol fuel represent over 40% of the energy produced by combustion of the ethanol. When such real world factors such as evaporative losses, transportation costs (which are elevated for low energy density fuels such as ethanol), and less than perfect combustion/energy transfer efficiency are factored in the costs of producing ethanol fuel from such processes become significant. With such high energy requirements the actual sustainability of ethanol as a fuel using such processes becomes subject to debate.

In processes of the inventive concept, a catalytic reactor is coupled to conventional alcohol separation process to generate fungible (i.e. interchangeable with petrochemical) transport fuels (such as diesel, gasoline, or jet fuels), in at least some embodiments along with gaseous light hydrocarbon products, from alcohol and water mixtures. Such a catalytic process can also be utilized to generate other chemicals such as benzene, toluene, and/or xylene products (i.e., BTX), along with other hydrocarbon fractions. The catalytic process utilizes elevated temperatures, and heat from reactor effluent can be heat integrated with several intermediate process streams to reduce overall plant heat requirements, GHG emission, and the use of fossil derived fuels.

It should be appreciated that while examples are provided in the context of conversion of ethanol provided by fermentation, other alcohol feedstocks can also be used. For example, methanol obtained from pyrolysis of lignocellulosic material and/or from synthesis gas generated from renewable sources (e.g. biomass) can be utilized as a feedstock in systems and methods of the inventive concept. Similarly, propanol and/or butanol derived from renewable sources, for example through the use of genetically modified microorganisms, can be used. In some embodiments two or more alcohol feedstocks can be combined prior to or on entry into systems and methods of the inventive concept. In such embodiments the combined alcohol feedstocks need not be of the same type. For example, an ethanol feedstock derived from grain fermentation can be combined with a methanol feedstock produced from synthesis gas derived from biomass. It should be appreciated that this capacity provides systems and methods of the inventive concept with process flexibility not present in the prior art. An example of a process of the inventive concept is shown in FIG. 2.

Unless the context dictates the contrary, all ranges set forth herein should be interpreted as being inclusive of their endpoints, and open-ended ranges should be interpreted to include only commercially practical values. Similarly, all lists of values should be considered as inclusive of intermediate values unless the context indicates the contrary. The recitation of ranges of values herein is merely intended to serve as a shorthand method of referring individually to each separate value falling within the range. Unless otherwise indicated herein, each individual value with a range is incorporated into the specification as if it were individually recited herein.

Figure 2:
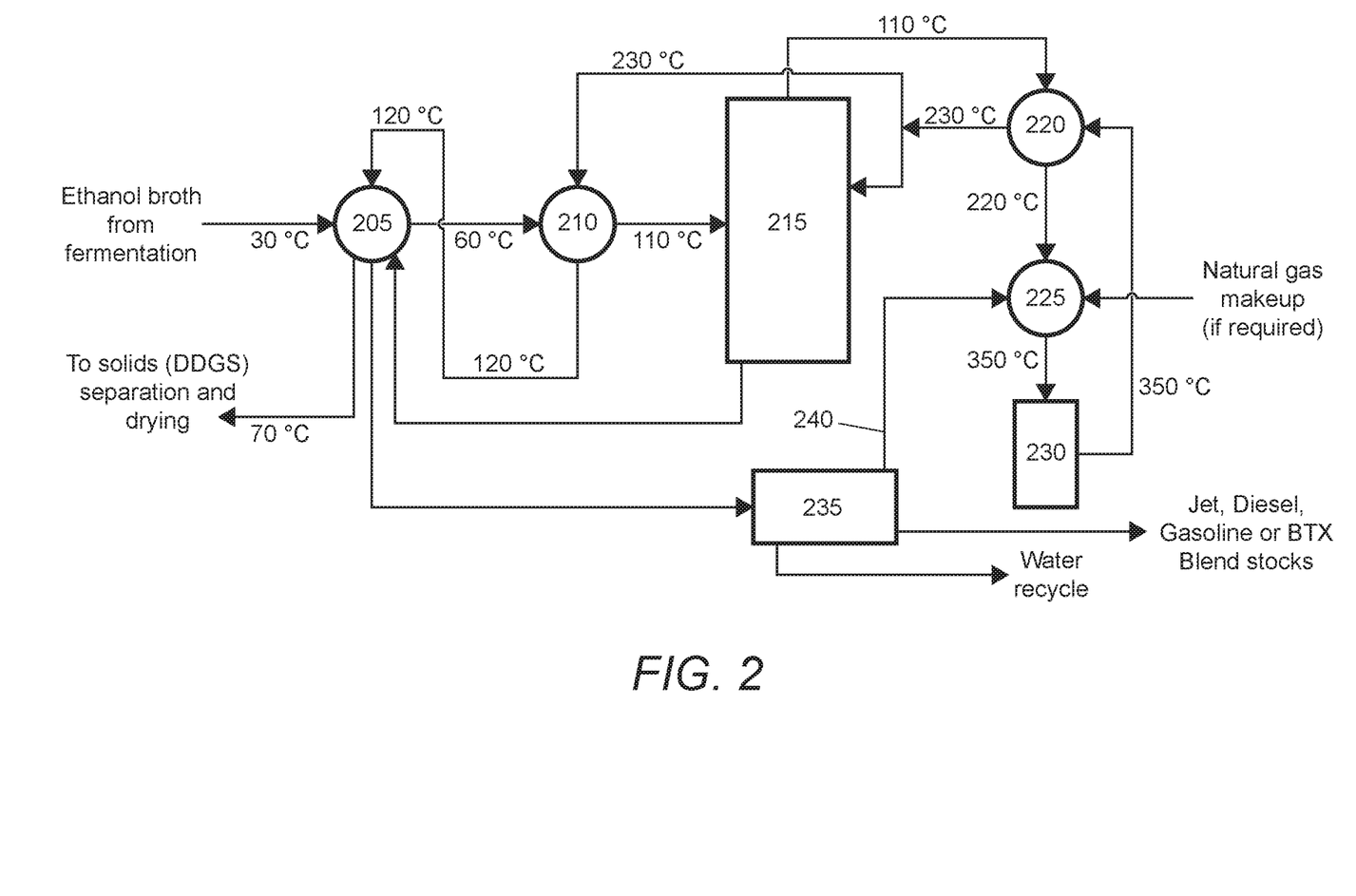
FIG. 2 schematically depicts an exemplary process of the inventive concept, in which a fermentation process (for example, production of ethanol via grain fermentation) is coupled to a catalytic process to convert ethanol to hydrocarbons, showing transfer of heat between various individual processes.

FIG. 2 schematically depicts an embodiment of a system of the inventive concept in which an alcohol production facility is coupled with a catalytic reactor, fermentation broth enters the process and is first heated, by a first beer column pre-heater 205. Such a fermentation broth can be an ethanol broth, however it should be appreciated that the fermentation broth can be an alcohol broth that includes methanol, ethanol, propanol, butanol, or a mixture of two or more of these. At least some of the heat for this process can be provided by the beer column 215 bottoms stream (which includes water and residual solids). At this point in the process solids can be removed from such a bottoms stream by any suitable method and be further processed (for example, as DDGs in corn ethanol production and/or solids for use as boiler fuel in cellulosic ethanol plants). Suitable methods for separation of these solids include decantation, settling, filtration, and centrifugation. In a preferred embodiment of the inventive concept solids are removed from the bottoms stream by a centrifuge or vortex device that permits continuous removal of solids from the bottoms stream.

The pre-heated alcohol broth can be transferred to a second beer column pre-heater 210 where it is further heated (for example, via heat exchange with a product stream from a catalytic reactor 230). In some embodiments of the inventive concept, a single beer column pre-heater can be utilized, and can receive heat from either of both of the bottoms stream from the beer column 215 and a product stream from the catalytic reactor 230. This heated alcohol broth can then be directed into a beer column 215, where alcohol (i.e. methanol, ethanol, butanol and/or propanol) is stripped from the alcohol broth as a concentrated alcohol/water stream (for example, a vapor). Such an alcohol/water stream can contain 10%, 20%, 30%, 40%, 50%, 60%, 70% or more alcohol by weight. In a preferred embodiment of the inventive concept such a concentrated alcohol/water stream contains 40-60% alcohol (w/w). As shown, bottom materials from the beer column 215 can be transferred to the first beer column pre-heater 205 to recover heat from this stream, thus lowering heating/energy requirements (i.e. via heat integration).

In some embodiments of the inventive concept the alcohol/water mixture from the beer column 215 can be directed to the catalytic reactor 230 without a change in composition. In other embodiments (not depicted), a rectifier or similar apparatus can be utilized to provide additional separation of alcohol from the alcohol/water mixture obtained from the beer column 215 to produce an alcohol-enriched alcohol/water stream that is directed to a catalytic reactor 230. In such an embodiment, the rectifier or similar apparatus would be interposed between and in fluid communication with the beer column 215 and the catalytic reactor 230. In either of such embodiments, the alcohol/water mixture can be transferred to reactor pre-heater 220, which raises the temperature of the alcohol/water mixture from about 110° C. to about 220° C. (for example, via heat exchange with a product stream of the catalytic reactor 230). Such a pre-heated alcohol/water mixture can then be transferred to a furnace 225, where it is heated to a temperature suitable for the catalytic reaction (for example, about 275° C. to about 350° C.). Output from furnace 225 is directed to a catalytic reactor 230, which produces a product stream that can include the desired fuel, BTX, or chemical product, water, and/or light hydrocarbon products at about 350° C.

The elevated temperature of the catalytic reactor 230 product stream represents a source of considerable thermal energy that can be utilized advantageously before it reaches a phase separator 235 (for example, a 3-phase decanter). A portion of this heat can be transferred to the alcohol/water mixture preheater 220, thereby reducing the temperature of the catalytic reactor product stream (for example, to about 230° C.). Similarly, a portion of the remaining heat can be transferred to the beer column 215 (e.g. to a reboiler) and/or to a second beer column pre-heater 210 to reduce or eliminate fuel consumption of these components, and further reduce the temperature of the catalytic reactor 230 product stream (for example, to about 120° C.). Remaining heat, or a portion thereof, can be transferred to a first beer column pre-heater 205, reducing or eliminating the fuel requirements for this process.

Following such heat integration steps, the product stream from the catalytic reactor 230 mixture is transferred to a phase separator 235, which separates the mixture into two or more product streams, for example (a) jet, diesel, gasoline, chemicals, or BTX hydrocarbon products that can be used directly, (b) water, which can be recycled (for example, into a fermentation process), and (c) light hydrocarbon 240 fractions. Suitable phase separators include decanters (such as a 3-phase decanter), centrifuges, and membrane separators. As shown, light hydrocarbon fractions 240 can be directed to the furnace 225, where combustion provides heat to the alcohol/water mixture. If available light hydrocarbon fractions are insufficient or if the light fraction has sufficient commercial value, additional fuel (for example, natural gas) can be supplied to either supplement or entirely provide for the system's heat requirements.

As shown, the heat energy in the catalytic reactor product stream can be heat integrated with multiple components of the process in order to reduce heating requirements during the transfer of the product+water mixture to a phase separator. As shown, the hot product+water mixture can be routed to provide heat to a reactor pre-heater, a beer column, a beer column heater, and/or a beer column pre-heater(s). This advantageously provides necessary heat to these components while eliminating or reducing the need for fuel, while at the same time cooling the product+water mixture to temperatures suitable for operation of a phase separator. Heat integration can be performed by any suitable means. Suitable means include heat exchanging assemblies that bring the product streams undergoing heat transfer into direct thermal communication. Alternatively heat can be transferred indirectly, for example through the use of a heat transfer medium that is in thermal communication with both a heat source stream and a heat destination stream, or through the use of a heat pipe. Alternatively, heat energy can be transformed into a different form of energy (for example, electrical power or mechanical work) at a heat source, transmitted to a heat destination, and transformed back into heat energy (for example by resistance heating or friction).

Such heat transfer, in combination with heat provided by combustion of light fraction products of the process, can provide all or part (e.g., about 30%, about 40%, about 50%, about 60%, about 70%, about 80%, about 90%, or more) of the heat necessary to support the overall process. In embodiments or implementations where the amount of heat provided by the product+water mixture leaving the catalytic reactor and combustion of light fraction products is not sufficient, the shortfall can be accommodated using natural gas, combustion of other suitable fuels, or transfer of heat from other processes (for example, processes external to the system of the inventive concept).

Due to the relative lack of fuel consuming distillation processes and transfer of heat from the output of the catalytic reactor, considerable energy savings are realized relative to prior art processes. For a typical plant utilizing systems and methods of the inventive concept, energy consumption per gallon of fuel produced is as follows: beer column pre-heater ~3,000 BTU, beer column ~10,000 BTU, furnace ~2,000 BTU. Overall, ~15,000 BTU are utilized per gallon of fuel produced. This represents a greater than 50% reduction in energy costs relative to prior art processes.

It should also be appreciated that the resulting products are energy dense fuels or high value organic solvents that can be utilized directly in current vehicles and processes without adaptation. As such, the approximately 15,000 BTU utilized per gallon of fuel produced by systems and processes of the inventive concept represents only about 12% of the energy contained in a gasoline or jet fuel product and about 11% of the energy contained in a diesel fuel product. As a result, systems and methods of the inventive concept truly enhance sustainable and economically viable production of fuels and/or BTX products from renewable sources such as grain.

Although the examples provided above focused on alcohol production from corn by so-called dry milling of corn, it should be appreciated that systems and methods of the inventive concept can be equally well applied to production of ethanol and other alcohols (for example, methanol, propanol, and butanol) by fermentation of sugar derived from sugar cane and/or other sugar sources; fermentation of sugar released by the breakdown of cellulosic or lignocellulosic biomass; alcohol production from corn by wet-mill and other processes; and/or production of ethanol or other alcohols by non-fermentation processes (e.g., chemical or biological mediated catalytic conversion of synthesis gas to ethanol). In some embodiments, alcohol from two or more alcohol sources can be combined and utilized in a process of the inventive concept. Such a combination can occur prior to introduction to the catalytic reactor and/or at the point of introduction to the catalytic reactor. In addition, it should be appreciated that the sequence and choice of operations can also be modified from those depicted in order to provide energy saving benefits.

In addition to consuming large amounts of energy, it should be appreciated that typical prior art processes (such as those depicted in FIG. 1) utilize large amounts of water. Water is lost from these systems at a number of points in the process, including: 1) evaporative losses from cooling towers associated with cooling effluents from separation columns, 2) evaporative losses associated with drying solids (e.g. DDGs), 3) boiler blowdown to avoid concentration of impurities from steam evaporation, and 4) leaks. It should be appreciated that water and energy consumption by various components of such a system can be significant. For a typical plant utilizing corn fermentation, net water consumption averages between 3 and 4 gallons of water for every gallon of fuel ethanol produced. Water consumption is greater in biochemical conversion of cellulosic feedstocks to ethanol, averaging approximately 6 gallons of water for every gallon of ethanol produced. Water consumption for thermochemical conversion of cellulosic biomass to ethanol is averages 1.9 gallons of water per gallon of ethanol.

Depending upon the starting material utilized to produce the ethanol broth and the conversion technology, water consumption in a typical prior art process ranges from 1.9-6 gallons of water per gallon of ethanol produced. With fresh water in increasingly short supply such high water requirements the sustainability of ethanol as a fuel using such prior art processes is doubtful.

As noted above, in processes of the inventive concept, a catalytic reactor can be coupled to conventional alcohol separation process to generate fungible (i.e. interchangeable with petrochemical products) transport fuels (such as diesel, gasoline, or jet fuels) from alcohol and water mixtures. In at least some embodiments gaseous light hydrocarbon products can additionally be produced. Such a catalytic process can also be utilized to generate other chemicals such as benzene, toluene, and/or xylene products (i.e., BTX), along with other hydrocarbon fractions (for example, light or gaseous fractions). The catalytic process utilizes elevated temperatures, and heat from reactor effluent can be heat integrated with several intermediate process streams to reduce overall plant heat requirements, GHG emission, and the use of fossil derived fuels. Systems and methods of the inventive concept also significantly reduce the water requirements of fuel production from sustainable alcohol feedstreams. An example of a system of the inventive concept is shown in FIG. 3.

Figure 3:
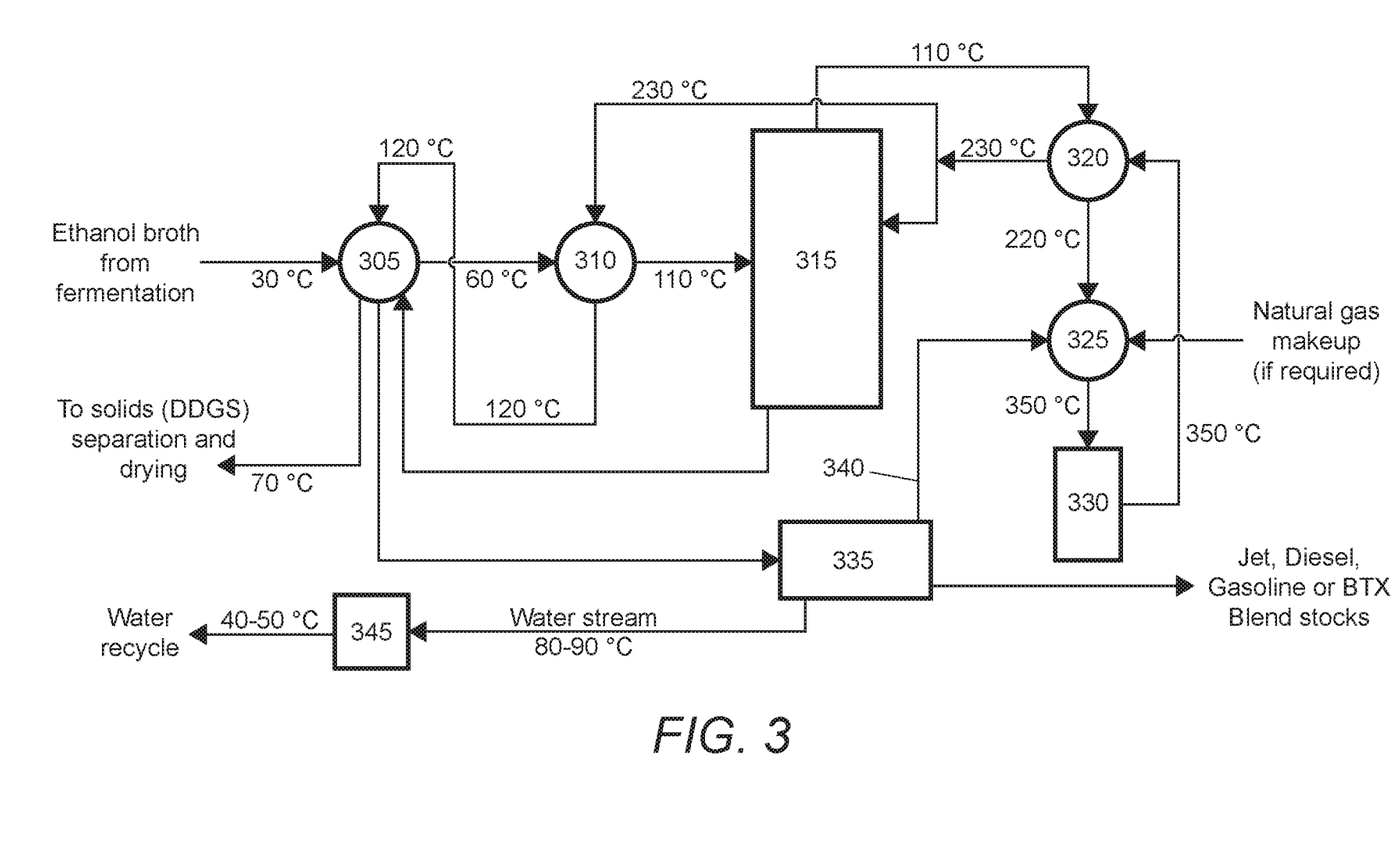
FIG. 3 schematically depicts another exemplary system of the inventive concept, in which a fermentation process (for example, production of ethanol via grain fermentation) is coupled to a catalytic process to convert alcohol to hydrocarbons, showing cooling and recycling of water produced in the catalytic process.

As shown in FIG. 3, in a system of the inventive concept in which an alcohol production facility is coupled with a catalytic reactor, fermentation or alcohol broth enters the process and is initially heated, for example in a first beer column preheater 305. Such a fermentation broth can be an ethanol broth, however it should be appreciated that the fermentation or alcohol broth can include methanol, ethanol, propanol, butanol, or a mixture of two or more of these. After passing through the first beer column preheater 305, the alcohol broth can be transferred to a second beer column preheater 310 for further heating. At least some of the heat for these processes can be transferred from a beer column 315 bottoms stream (which typically includes water and residual solids). Process solids can be removed from such a bottoms stream (for example by centrifugation or filtration) and be further processed. For example, such recovered solids can be utilized as DDGs in corn ethanol production and/or solids for use as boiler fuel in cellulosic ethanol plants. In some embodiments of the inventive concept, a single beer column pre-heater can be utilized, and can receive heat from either or both of the bottoms stream from the beer column 315 and a product stream from a catalytic reactor 330.

The heated alcohol broth can then be directed into a beer column 315, where alcohol (e.g. methanol, ethanol, butanol and/or propanol) is stripped from the alcohol broth as a concentrated alcohol/water stream. Such an alcohol/water stream can contain 10%, 20%, 30%, 40%, 50%, 60%, 70% or more alcohol by weight. In a preferred embodiment of the inventive concept such a concentrated alcohol/water stream contains 40-60% alcohol (w/w), and can be in the form of a vapor. The alcohol/water mixture is transferred to a reactor pre-heater 320, which raises the temperature of the ethanol/water mixture from about 110° C. to about 220° C. The pre-heated alcohol/water mixture is then transferred to a furnace 325, where it is heated to a temperature suitable for the catalytic reaction (for example, about 350° C.). Output from the furnace 325 is directed to the catalytic reactor 330, which produces the desired fuel, BTX or other chemical product mixed with water at about 350° C.

In some embodiments of the inventive concept the alcohol/water mixture from the beer column 315 can be directed to the catalytic reactor 330 without a change in composition. In other embodiments (not depicted), a rectifier or similar apparatus can be utilized to provide additional separation of alcohol from the alcohol/water mixture obtained from the beer column 315 to produce an alcohol-enriched alcohol/water stream that is directed to a catalytic reactor 330. In such an embodiment, the rectifier or similar apparatus would be interposed between and in fluid communication with the beer column 315 and the catalytic reactor 330. In either of such embodiments, the alcohol/water mixture can be transferred to reactor pre-heater 320, which raises the temperature of the alcohol/water mixture from about 110° C. to about 220° C. (for example, via heat exchange with a product stream of the catalytic reactor 330). Such a pre-heated alcohol/water mixture can then be transferred to a furnace 325, where it is heated to a temperature suitable for the catalytic reaction (for example, about 275° C. to about 350° C.). Output from furnace 325 is directed to a catalytic reactor 330, which produces a product stream that can include the desired fuel, BTX, or chemical product, water, and/or light hydrocarbon 340 products at about 350° C.

The elevated temperature of the output of the catalytic reactor 330 represents a source of considerable thermal energy that can be utilized advantageously before it reaches a phase separator 335 (for example, a 3-phase decanter). A portion of this heat can be transferred to the alcohol/water mixture preheater 320, thereby reducing the temperature of the catalytic reactor stream (for example, to about 230° C.). Similarly, a portion of the remaining heat can be transferred to the beer column 315 (e.g. to a reboiler) and/or to a second beer column pre-heater 310, rectifier reboiler, and other processes requiring heat (e.g. plant water input) to reduce or eliminate fuel consumption of these components, and further reduce the temperature of the catalytic reactor 330 product stream (for example, to about 120° C.). Remaining heat, or a portion thereof, can be transferred to the beer column pre-heater 305, reducing or eliminating the fuel requirements for this process.

Following such heat integration steps, the product stream from the catalytic reactor 330 mixture can be transferred to a phase separator 335 (for example, a 3-phase decanter), which separates the mixture into at least three products streams: (a) jet, diesel, gasoline, chemicals, or BTX hydrocarbon products that can be used directly, (b) hot (for example, about 80° C. to 90° C.) water, which can be recycled (for example, into a fermentation process), and in some embodiments (c) light hydrocarbon fractions 340. The hot water stream can be re-used as is, or it can be cooled (for example, to 40-50° C.) in order to reduce evaporative losses. Such cooling can be provided by a passive device, such as a radiator 345 or similar device. Alternatively, heat from the hot water stream can be transferred to a thermal mass during daytime operations, followed by cessation of heat transfer and passive cooling of the thermal mass at night. Such heat transfers can be direct (i.e. through direct thermal communication) or indirect. Indirect heat transfers can be accomplished using a heat transfer medium and/or heat transfer device (e.g. a heat pipe). In still another embodiment heat can be transferred from the hot water stream by earth coupling. As shown, light hydrocarbon fractions 340 can be directed to the furnace 325, where combustion provides heat to the alcohol/water mixture. If available light hydrocarbon fractions are insufficient or if the light fraction has sufficient commercial value, additional fuel (for example, natural gas) can be supplied to either supplement or entirely provide for the system's heat requirements.

As shown, the heat energy in the catalytic reactor product stream can be heat integrated with multiple components of the process in order to reduce heating requirements during the transfer of the product+water mixture to a phase separator. As shown, the hot product+water mixture can be routed to provide heat to a reactor pre-heater, a beer column, a beer column heater/reboiler, and/or a beer column preheater(s). In other embodiments, the hot product+water mixture can be used to reduce heat requirements in a rectification column. This advantageously provides necessary heat to these components while eliminating or reducing the need for fuel, while at the same time cooling the product+water mixture to temperatures suitable for operation of a phase separator. Such heat transfer, in combination with heat provided by combustion of light fraction products of the process, can provide all or part (e.g., about 30%, about 40%, about 50%, about 60%, about 70%, about 80%, about 90%, or more) of the heat necessary to support the overall process. In embodiments or implementations where the amount of heat provided by the product+water mixture leaving the catalytic reactor and combustion of light fraction products is not sufficient, the shortfall can be accommodated using natural gas, combustion of other suitable fuels, or transfer of heat from other processes (for example, processes external to the system of the inventive concept).

In some embodiments of the inventive process, heat contained in the hot water stream is transferred to other components of the system in order to reduce energy consumption and to reduce the temperature of the recycled water (thereby reducing evaporative losses, for example from cooling towers). An example of such an embodiment is shown schematically in FIG. 4.

Figure 4:
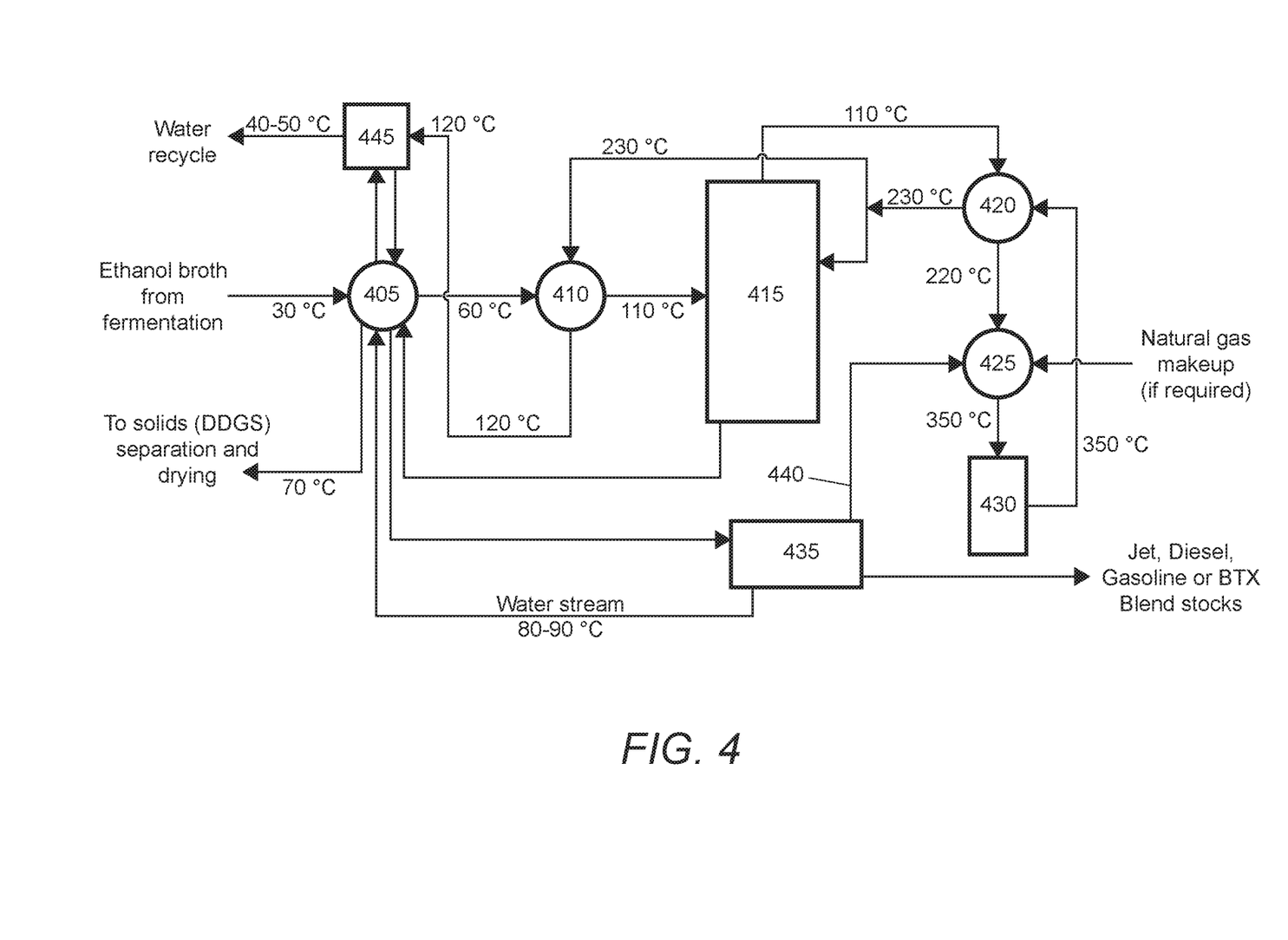
FIG. 4 schematically depicts another exemplary system of the inventive concept, in which a fermentation process (for example, production of ethanol via grain fermentation) is coupled to a catalytic process to convert alcohol to hydrocarbons.

As shown in FIG. 4, fermentation provides an alcohol broth, which can be heated in first and second beer column preheaters (405 and 410, respectively) as described above. The pre-heated alcohol broth is then transferred to a beer column 415, where alcohol is stripped from the alcohol broth in the form of a concentrated alcohol/water mixture containing 10%, 20%, 30%, 40%, 50%, or more alcohol (w/w). As shown, residual materials from this process can be transferred from the bottom of the beer column to the second beer column pre-heater 410 for repeated extraction in order to improve efficiency. As described above in the description of the system depicted in FIG. 3, in some embodiments a single beer column pre-heater can be used. The concentrated alcohol/water mixture from the beer column is transferred to a reactor pre-heater 420, which raises the temperature of the alcohol/water mixture from about 110° C. to about 220° C. The pre-heated alcohol/water mixture is then transferred to a furnace 425, where it is heated to a temperature suitable for the catalytic reaction (for example, about 350° C.). Output from the furnace 425 is directed to a catalytic reactor 430, which produces the desired fuel or BTX product mixed with water (and in some embodiments, a light hydrocarbon fraction 440) at about 350° C.

The elevated temperature of the output of the catalytic reactor 430 represents a source of considerable thermal energy that can be utilized as it is transferred to a 3-phase decanter 435. A portion of this heat can be transferred to the reactor preheater 420, thereby reducing the temperature of the catalytic reactor output to about 230° C. Similarly, a portion of the remaining heat can be transferred to the beer column 415 and/or to the second beer column heater 410 to reduce or eliminate fuel consumption of these components, and further reduce the temperature of the product mixture from the reactor (for example, to about 120° C.). Remaining heat, or a portion thereof, can be transferred to the first beer column pre-heater 405, reducing or eliminating the fuel requirements for this process.

The output of the catalytic reactor 430 mixture can be transferred to a phase separator 435, which separates the mixture into different products streams: (a) a hot (for example, 80° C. to 90° C.) water stream, (b) jet, diesel, gasoline fuel products or BTX products that can be used directly, and, in some embodiments, (c) light hydrocarbon fractions 440. Heat from the hot water stream can be transferred to other processes in the system in order to reduce energy costs while reducing the temperature of the hot water stream. As shown in FIG. 4, heat can be transferred from the hot water stream to the first beer column pre-heater 405. In some embodiments, heat transfer to other system components, radiative cooling, and/or active cooling (for example, in an absorption cooler) can be utilized in individually or in combination to reduce the temperature of the hot water stream. Suitable active cooling methods include use of an absorption cooler, use of an Einstein refrigerator, withdrawal of heat using a heat engine, and withdrawal of heat using the thermoelectric effect. In some embodiments the temperature of the hot water stream can be reduced by passage through an absorption cooler 445. Such an absorption cooler 445 can be driven, at least in part, by heat transferred from an intermediate process stream of the system. Such an embodiment is depicted in FIG. 4, in which heat from the output of the catalytic reactor 430 is so utilized. In other embodiments heat from burning fuel (such as natural gas and/or light hydrocarbon fractions 440 from the alcohol conversion process) can be used to supplement or replace heat transfer from a system process stream to the absorption cooler 445. Such treatment can reduce the temperature of the hot water stream (for example to about 40° C. to 50° C.) and thereby reduce water losses due to evaporation. As shown, light hydrocarbon fractions 440 can be directed to the furnace 425, where combustion provides heat to the alcohol/water mixture. If available light hydrocarbon fractions are insufficient, natural gas can be provided as additional fuel to heat the furnace 425.

Due to the relative lack of water and fuel consuming distillation processes, lack of use of molecular sieves, and transfer of heat from various process streams, considerable water and energy savings are realized relative to prior art processes. Systems of the inventive process provide reduced water consumption by at least two different methods. In some embodiments, the lack of a rectifier (which represents a major source of water loss in prior art systems) can reduce water consumption by systems of the inventive concept by 20% or more compared to prior art processes. Some water is also lost during processing using molecular sieves in prior art processes; such devices are not necessary in systems and methods of the inventive concept. Water savings produced by recycling of water generated by the ethanol conversion process typically range from 5% to 15% or more over prior art processes. With corn ethanol plants currently producing approximately 15 billion gallons of ethanol annually, this can reduce the water consumption of plants utilizing corn fermentation by approximately 4.5 to 6 billion or more gallons a year or more annually via water generation during the ethanol conversion process, and by approximately 11.3 to 20 billion gallons or more of water a year annually when savings due to the lack of rectifiers are included.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A system for producing a hydrocarbon product, comprising:
   a source of alcohol broth that is in fluid communication with a primary beer column pre-heater;
   a beer column configured to receive a heated alcohol broth from the primary beer column pre-heater and to produce a first intermediate product stream comprising an alcohol/water mixture and a second intermediate product stream comprising residual matter;
   a reactor pre-heater that is in fluid communication with the beer column and is configured to receive the first intermediate product stream and heat it to produce a pre-heated first intermediate product stream;
   a furnace that is in fluid communication with the reactor pre-heater, and is configured to receive the pre-heated first intermediate product stream and heat it to at least 250° C. to produce a heated first intermediate product stream;
   a catalytic reactor that is in fluid communication with the furnace and is configured to generate a third intermediate product stream comprising a hydrocarbon product, water, and a light hydrocarbon;
   a first conduit that is configured to direct the third intermediate product stream to a phase separator, wherein the conduit is configured to transfer at least a portion of heat energy of the third intermediate product stream to the reactor pre-heater, and wherein the phase separator is configured to separate the third intermediate product stream into a hydrocarbon product stream comprising the hydrocarbon product, a water stream, and a light hydrocarbon fraction stream.

2. The system of claim 1, further comprising a second conduit in fluid communication with the phase separator and configured to direct at least a portion of the light hydrocarbon fraction stream to the furnace.

3. The system of claim 1, wherein the hydrocarbon product is selected from the group consisting of gasoline, diesel fuel, jet fuel, chemicals, and a BTX product.

4. The method of claim 1, further comprising a source of natural gas that is in fluidic communication with the furnace.

5. The system of claim 1, wherein the first conduit is configured to transfer heat from the third intermediate product stream to the primary beer column pre-heater.

6. The system of claim 1, further comprising a preliminary beer column pre-heater that is interposed between and in fluid communication with the source of alcohol broth and the primary beer column pre-heater.

7. The system of claim 6, wherein the first conduit is configured to transfer heat from the third intermediate product stream to the preliminary beer column pre-heater.

8. The system of claim 1, wherein energy supplied to the system in the production of a volume of the hydrocarbon product represents less than 20% of energy obtained on combustion of the volume of hydrocarbon product.

9. The system of claim 1, wherein the water stream is provided to a fermentation process.

10. The system of claim 1, further comprising a third conduit that is in fluidic communication with the beer column, wherein the third conduit is configured to return at least a portion of the second intermediate process stream to the beer column.

11. A system for reducing water consumption in a fuel plant comprising;
   a source of an alcohol broth comprising an alcohol;
   a primary beer column pre-heater that is in fluid communication with the source of the alcohol broth;
   a beer column that is in fluid communication with the primary beer column pre-heater, wherein the beer column is configured to generate a first intermediate product stream comprising a concentrated alcohol/water mixture;
   a catalytic unit pre-heater that is in fluid communication with the beer column, and that is configured to receive the concentrated alcohol/water mixture and to generate a pre-heated alcohol/water mixture;

an oven that is in fluid communication with the catalytic unit pre-heater and that is configured to receive the pre-heated alcohol/water mixture and generate a heated alcohol/water mixture;

a catalytic unit that is in fluid communication with the oven and that is configured to receive the heated alcohol/water mixture and to generate a second intermediate product stream comprising water and a hydrocarbon product;

a phase separator that is in fluid communication with the catalytic unit and configured to receive the second intermediate product stream and to separate the second intermediate product stream into a hot water stream and a hydrocarbon product stream; and a first conduit that is in fluid communication with the phase separator and configured to transfer at least a portion of the hot water stream for recycling.

12. The system of claim 11, further comprising a cooling unit that is in fluid communication with the first conduit and that is configured to generate a cooled water stream.

13. The system of claim 12, wherein the cooling unit comprises a radiative cooler.

14. The system of claim 12, wherein the cooling unit comprises an absorption cooler.

15. The system of claim 14, further comprising a second conduit that is in fluid communication with the catalytic reactor and the phase separator, and that is configured to transfer the second intermediate product from the catalytic reactor to the phase separator while transferring at least part of the heat contained in the second intermediate product to the absorption cooler.

16. The system of claim 14, wherein the second intermediate product stream further comprises a light hydrocarbon fraction and wherein the phase separator is configured to separate a light hydrocarbon stream from the hydrocarbon product stream and from the hot water stream.

17. The system of claim 16 further comprising a third conduit, wherein the third conduit is in fluid communication with the phase separator and the oven, and wherein the third conduit is configured to transfer at least a portion of the light hydrocarbon stream from the phase separator to the oven.

18. The system of claim 11, wherein the catalytic unit is configured to generate at least one mole of water for every mole of alcohol that is converted to hydrocarbon.

19. The system of claim 11, further comprising a secondary beer column pre-heater interposed between the source of the alcohol broth and the primary beer column pre-heater, wherein the beer column pre-heater is in fluid communication with the source of the alcohol broth and the primary beer column pre-heater.

20. The system of claim 19, wherein the first conduit is configured to transfer at least a portion of the heat contained in the hot water stream to the secondary beer column pre-heater.

21. The system of claim 19, further comprising:

a fourth conduit that is in fluid communication with the catalytic unit and the phase separator and configured to receive the second intermediate product stream from the catalytic unit, wherein the first conduit is configured to transfer at least a portion of the heat contained in the hot water stream to the secondary beer column pre-heater, and wherein the fourth conduit is configured to transfer at least a portion of the heat energy contained in the second intermediate product stream to the secondary beer column pre-heater.

* * * * *